Figure 1:
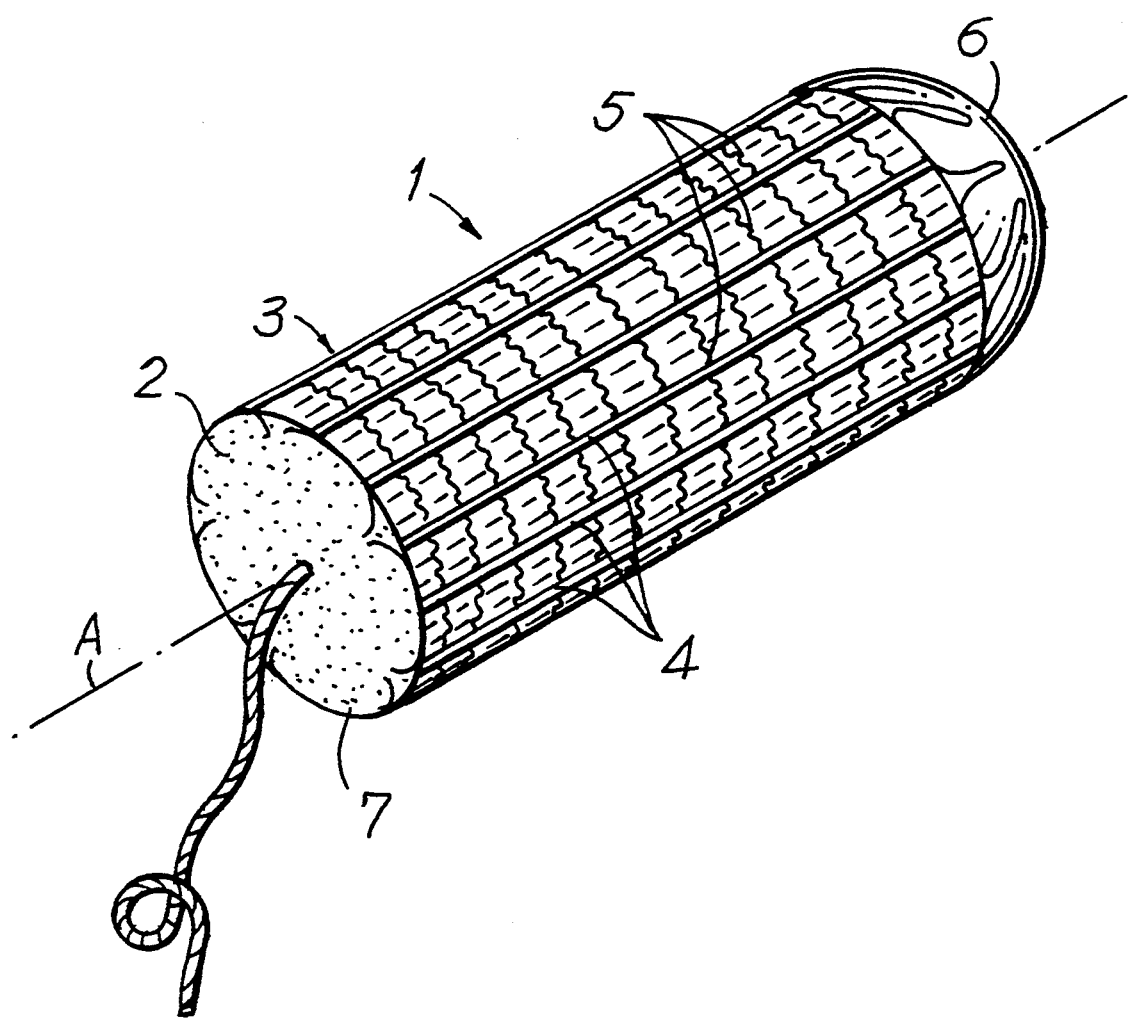

United States Patent [19]

Lloyd et al.

[11] Patent Number: 5,374,258
[45] Date of Patent: Dec. 20, 1994

[54] TAMPONS

[75] Inventors: Ronald Lloyd, Sawbridgeworth; Karen A. Stringer, Birmingham, both of United Kingdom

[73] Assignee: Smith & Nephew plc, United Kingdom

[21] Appl. No.: 488,060

[22] PCT Filed: Dec. 15, 1988

[86] PCT No.: PCT/GB88/01114

§ 371 Date: Sep. 20, 1990

§ 102(e) Date: Sep. 20, 1990

[87] PCT Pub. No.: WO89/05621

PCT Pub. Date: Jun. 29, 1989

[30] Foreign Application Priority Data

Dec. 15, 1987 [GB] United Kingdom ............... 8729205

[51] Int. Cl.⁵ .................................... A61F 13/15
[52] U.S. Cl. ..................... 604/358; 604/904; 604/363
[58] Field of Search .............. 604/385.1, 904, 365, 604/358, 375, 363

[56] References Cited

U.S. PATENT DOCUMENTS

| 1,503,359 | 7/1924 | Fabricius-Bjerre | 604/904 |
| 1,932,383 | 10/1933 | Richardson | 604/363 |
| 2,965,101 | 12/1960 | Schirmer et al. | 604/385.1 |
| 3,058,469 | 10/1962 | Crockford | 604/363 |
| 3,683,912 | 8/1972 | Olson et al. | 604/904 |
| 3,856,143 | 12/1974 | Simon et al. | 604/358 |
| 3,946,737 | 3/1976 | Kobler | 604/385.1 |
| 3,986,511 | 10/1976 | Olofsson et al. | 604/385.1 |
| 4,135,021 | 1/1979 | Patchell et al. | 604/369 |
| 4,175,561 | 11/1979 | Hirschman | 128/296 |
| 4,211,225 | 7/1980 | Sibalis | 128/285 |
| 4,291,696 | 9/1981 | Ring | 604/904 |
| 4,294,253 | 10/1981 | Friese | 604/385.1 |
| 4,351,339 | 9/1982 | Sneider | 604/385.1 |
| 4,533,356 | 8/1985 | Bengmark et al. | 604/358 |
| 4,624,668 | 11/1986 | Siegers | 604/358 |
| 4,661,101 | 4/1987 | Sustmann | 604/360 |
| 4,705,514 | 11/1987 | Barnard | 604/358 |
| 4,743,237 | 5/1988 | Sweere | 604/358 |

FOREIGN PATENT DOCUMENTS 1548865 7/1979 United Kingdom .

Primary Examiner—Randall L. Green
Assistant Examiner—Rob Clarke
Attorney, Agent, or Firm—Rosenman & Colin

[57] ABSTRACT

A tampon for hygienic use which comprises an absorbent core of general cylindrical shape having a liquid pervious cover layer is disclosed. The cover layer is a plastics material which comprises parallel ribs in one direction interconnected by a plurality of fibrillated strands in the transverse direction. The ribs of the cover layer lie in a direction which is in a direction parallel to the main axis of the tampon.

16 Claims, 1 Drawing Sheet

TAMPONS

The present invention relates to tampons for hygienic use and to processes for their preparation.

Conventional tampons for hygienic use normally comprise an absorbent core containing hydrophilic material such as hydrophilic foam or fibres which has been formed into general cylindrical shape by for example compressing or moulding. Conventional tampons, however, have been found to be relatively uncomfortable to insert into the vagina due to the "dry feel" and abrasiveness of the absorbent fibre or foam surface of the absorbent core of these tampons. Furthermore conventional tampons which comprise an absorbent core containing hydrophobic cellulose fibres such as wood pulp fibres tend to shed these fibres when the absorbent core becomes moist in use, and in particular during insertion or removal of the tampon from the vagina. It is known from the disclosure of European Patent No. 149155 and United Kingdom Patent NOs. 1218641 and 2010680 that the absorbent core of tampons of this type can be provided with a liquid pervious non-woven fabric cover layer to inhibit in use shedding of fibres from the absorbent core. It is further disclosed in the aforementioned European Patent No. 149155 that such a non-woven fabric cover layer can also render the tampon more comfortable to insert into the vagina because the smoother nature of the non-woven fabric reduces the surface drag or resistance of the tampon during insertion. It has now been found that similar advantages can be obtained using an alternative cover layer material over the absorbent core of a tampon.

Accordingly the present invention provides a tampon for hygienic use which comprises an absorbent core of general cylindrical shape having a liquid pervious cover layer wherein the cover layer is a plastics material which comprises parallel ribs in one direction interconnected by a plurality of fibrillated strands in the transverse direction and wherein the ribs of the cover layer lie in a direction parallel to the main axis of the tampon.

FIG. 1 is an isometric view of a tampon, in accordance with the present invention.

Suitable plastics materials for use in the invention include those plastics materials disclosed in United Kingdom Patent No. 1548865 the disclosure of which is incorporated herein by cross reference. These plastics materials have thicker relatively smooth ribs interconnected by thinner fibrillated strands which provide the plastics materials with a smooth or soft feel in the direction of the ribs. A cover layer of such plastics material will therefore advantageously provide the absorbent core of a tampon of the invention with a smooth feel in the longitudinal direction thereof thereby rendering the tampon more comfortable to insert or withdraw from the vagina.

The plastics material has holes defined by the interconnected ribs and strands of the material. The size of the holes will therefore depend on density of ribs and strands in the material.

The plastics material can suitably have 4 to 20 ribs/cm and can preferably have 5 to 15 ribs/cm. Similarly the plastics material can suitably have 8 to 50 fibrillated strands/cm and can preferably have 10 to 40 fibrillated strands/cm.

It has been found that densities of ribs and fibrillated strands within the hereinabove ranges can provide a plastics material with holes which are sufficiently small to inhibit penetration of the material by moist fibres. Such a plastics material when used as a cover layer over the absorbent core of a tampon of the invention will therefore advantageously inhibit shedding of fibres from the absorbent core during use.

Suitably the plastics materials for use in the invention can have a weight per unit area of 2 to 30 g/m$^2$, desirably a weight per unit area of 2 to 20 g/m$^2$ and can preferably have a weight per unit area of 4 to 12 g/m$^2$.

Suitably plastics materials for use in the invention can have thickness of 0.03 mm to 0.15 mm and preferably have a thickness of 0.04 mm to 0.10 mm.

The plastics materials used in the invention will normally comprise a polymer which is relatively non-water absorbent to provide the tampon of the invention with a cover layer which similarly non-water absorbent. The polymer is preferably a thermoplastic polymer such as a polyolefine, polyamide or polystyrene to render the plastics material advantageously heat sealable.

The plastics materials used in the invention preferably a blend of incompatible polymers. Suitable blends comprise a major proportion of a polyolefine such as polypropylene, high density polyethylene or ethylene—propylene copolymers and a minor proportion of an incompatible polymer such as polystyrene, for example high impact polystyrene or polyamide.

An "incompatible polymer" is a polymer which in a blend therewith is not miscible with the polyolefine polymer. In such a blend the polymers would form separate phases and the polymer in the lower concentration (normally the incompatible polymer) would form a discrete disperse phase and the polymer present in the higher concentration (normally the polyolefine polymer) would form a continous phase.

Favoured plastics materials for use in the invention comprise a blend of high density polyethylene with 5 to 20% by weight of high impact polystyrene.

Apt plastics materials for use in the invention which comprise a blend of high density polyethylene with 8 to 10% by weight of high impact polystyrene, have a weight per unit area of 5 to 11 g/m$^2$ and a thickness 0.40 to 0.120 mm are known as net 909 (Trade mark) grades A4, A7, 48C and DHM available from Smith and Nephew Plastics Ltd.

The plastics material can advantageously be a composite material which comprises a substrate layer of higher melting point polymer and a heat sealable layer of a lower melting point polymer. Suitable plastics material of this type are given in United Kingdom Patent No. 2142246.

The absorbent core of the tampon of the invention will normally comprise a hydrophilic material such as hydrophilic fibres or hydrophilic foam. Suitable hydrophilic fibres include conventional hydrophilic cellulosic fibres such as wood pulp viscose or cotton fibres. A minor amount of hydrophobic fibres however may be present in the absorbent core.

The absorbent core of the tampon will preferably comprise compressed hydrophilic fibres to render the tampon expandible during use. Favoured tampons of this type expand in a lateral direction in use. Preferred lateral expanding tampons comprise a radially compressed spirally wound strip of hydrophilic fibres. Tampons of this type are disclosed in aforementioned European Patent No. 149155.

The cover layer of plastics material can cover the whole of the surface of the absorbent core of tampon. It is preferred however that the cover layer of plastics material covers only the side surface of the absorbent core.

The cover layer of plastics material can advantageously be attached to the surface of the absorbent core to inhibit displacement of the layer during insertion or withdrawal of the tampon. The cover layer can be attached to the surface of the absorbent core by means of a conventional bonding method such as adhesive bonding or preferably heat bonding. The plastics materials for example in the form of a strip may heat bonded to the surface of the absorbent core over the whole or preferably over a part of its area or length. The bonded area may be continuous or discontinuous portion for example in the form of strips or dots.

The tampon of the invention can optionally be provided with a rounded insertion end to facilitate insertion of the tampon into the vagina.

The tampon can be packaged in a conventional over wrap for use as a digital tampon or within an applicator package for insertion by means of an applicator.

In another aspect the present invention provides a process for forming a tampon of the invention which comprises spirally winding a strip of absorbent material which is attached at an end portion thereof to a strip of liquid pervious material and radially compressing the wound strip to form a tampon which comprises an absorbent core of general cylindrical shape having a cover layer of the liquid pervious material wherein the liquid pervious material is a plastics material which comprises parallel ribs in one direction interconnected by a plurality of fibrillated strands in the transverse direction and the ribs of the plastics material lie in the longitudinal direction of the tampon.

The strip of absorbent material will normally have a width similar to that of the length of the formed tampon. The strip of liquid pervious material may be wider than the strip of absorbent material to ensure that the liquid pervious material covers one or both ends of the wound strip.

It is preferred however that the width of the strip in the same or less than the width of the strip of absorbent material to ensure that the liquid pervious material covers only the side surface of the wound strip.

The parallel ribs in the strip of liquid pervious material will normally lie in the transverse direction of the strip to ensure that the parallel ribs of the liquid pervious material cover layer on the tampon lies in the longitudinal direction of the tampon.

The strip of liquid pervious material can be attached to the strap of absorbent material by any convenient bonding method such as adhesive or heat bonding. It is preferred that a heat bonding method is used. Suitable bonding methods include those given aforementioned European Patent No. 149155.

The strip of liquid pervious material will be attached to end portion of the strip of absorbent material. The end portion will have a length which is at least 10% desirably at least 30% and preferably at least 75% for example 90% of the length of liquid pervious material.

The combined strip can be spirally wound by a conventional method such as the methods disclosed in European Patent No 149155 and United Kingdom Patent NO. 1392995.

The strip of liquid pervious material will have a length which is sufficient to cover the wound strip and preferably length which is sufficient to overlap the attached portion thereof.

The unattached end portion of the wound strip of liquid pervious material which overlaps the attached portion thereof and can be then bonded to the back of this portion by a suitable method for example heat bonding to secure the wound strip. The wound strip can be radially compressed by a conventional method such as the methods disclosed in European Patent No. 149155 and United Kingdom No. 1082440 to form a tampon of the invention.

The tampon may be provided with a rounded end by conventional method such as the method disclosed in United Kingdom No. 1046066.

With respect to the drawing, FIG. 1 shows a tampon 1 having an absorbent core of generally cylindrical shape. The core 2 has a longitudinally extending main axis A. Surrounding core 2 is a liquid pervious cover 3 having ribs 4 that lie in a direction parallel to the main axis A and that are interconnected by fibrillated strands 5 that lie in a direction transverse to the main axis A. As shown, the cover layer 3 covers only the cylindrical surface of the core 2 and lies between the end portions 6, 7. A cord is secured to end portion 7.

EXAMPLE

A strip of liquid pervious plastics material (length 110 mm width 48 mm) was attached at a overlap end portion (length 30 mm) by heat sealing the one end of a strip (with 52 mm length 250 mm) of viscose fibres and the combined strip spirally wound to form an absorbent core of general cylindrical shape having a cover layer of the plastics material over its side surface. The non-attached end portion (length 16 mm) of the plastics material was then heat sealed over the attached end portion to hold the cover layer in place. The core and cover layer was then radially compressed to form a tampon of the invention (diameter 14–17 mm).

The plastics material used in this Example (known as net 909 ref H80) had 11/cm longitudinal parallel straight ribs interconnected by approximately 15/cm fibrillated strands and had a weight per unit area of 9 g/m$^2$. The ribs of the plastics material were in the longitudinal direction of the tampon. The strip was spirally wound by the method given in United Kingdom Patent No. 1392995 and the wound strip radially compressed by the method given in United Kingdom No. 1082770.

In a subjective test, it was found that tampons of the invention were significantly better with respect to ease of insertion and withdrawal at both the beginning and end of menstruation than tampons of similar construction but not provided with a cover layer.

We claim:

1. A tampon for hygienic use which comprises an absorbent core of general cylindrical shape having a main axis, said absorbent core having a liquid pervious cover layer wherein the cover layer is a plastics material having ribs which lie in a direction parallel to the main axis of the core and are interconnected by a plurality of fibrillated strands in a direction transverse to the main axis of the core.

2. A tampon as claimed in claim 1 in which the plastics material comprises a polyolefin.

3. A tampon as claimed in claim 2 in which the plastics material is a blend which comprises a major proportion of polyolefin and a minor proportion of an incompatible polymer.

4. A tampon as claimed in claim 3 in which the plastics material is a blend of high density polyethylene and polystyrene.

5. A tampon as claimed in claim 4 in which the blend contains 5 to 20% by weight of high impact polystyrene.

6. A tampon as claimed in claim 1 in which the plastics material has 5 to 15 ribs/cm and 10 to 40 fibrillated strands/cm.

7. A tampon as claimed in claim 1 in which the plastics material has a weight per unit area of 2 to 20 g/m$^2$.

8. A tampon as claimed in claim 1 in which the plastics material is a composite material comprising a substrate layer of higher melting point polymer and a heat sealable layer of lower melting point polymer.

9. A tampon as claimed in claim 1 having two end portions with said absorbent core being between said end portions, and a cylindrical surface in which the cover layer of plastics material covers only the cylindrical surface of the absorbent core of the tampon.

10. A tampon as claimed in claim 1 in which the absorbent core comprises a radially compressed spirally wound strip of hydrophilic fibres.

11. A tampon as claimed in claim 1 in which the cover layer is a strip of ribbed plastics material attached to the cylindrical surface of the absorbent core of the tampon.

12. A process for forming a tampon as claimed in claim 1 which comprises spirally winding a strip of absorbent material which is attached at an end portion thereof to a strip of liquid pervious material having a width and a length and radially compressing the wound strip to form a tampon which comprises a core of general cylindrical shape having a cover layer of the liquid pervious material wherein the liquid pervious material is a plastics material which comprises parallel ribs in one direction interconnected by a plurality of fibrillated strands in the transverse direction and the ribs of the plastics material lie in a direction parallel to the main axis of the tampon.

13. A process as claimed in claim 12 in which the strip of liquid pervious material is the same or less than the width of the strip of absorbent material to ensure that the liquid pervious material covers only the surface of the wound strip of absorbent material between the ends thereof.

14. A process as claimed in claim 12 in which the end portion attached to the strip of absorbent material has a length which is at least 30% of the length of the strip of liquid pervious material.

15. A process as claimed in claim 12 in which the strip of liquid pervious material is attached to the end portion of the strip of absorbent material by heat bonding.

16. A process as claimed in claim 12 in which the wound strip of liquid pervious material has an attached end overlapping the attached end portion thereof and is attached thereto by heat bonding.

* * * * *